(12) United States Patent  
Makrides

(10) Patent No.: US 9,121,773 B2  
(45) Date of Patent: Sep. 1, 2015

(54) GAS SENSORS AND METHODS OF CALIBRATING SAME

(71) Applicant: Bascom-Turner Instruments, Inc., Norwood, MA (US)

(72) Inventor: Alkis C. Makrides, Newton, MA (US)

(73) Assignee: Bascom-Turner Instruments, Norwood, MA (US)

( * ) Notice: Subject to any disclaimer, the term of this patent is extended or adjusted under 35 U.S.C. 154(b) by 237 days.

(21) Appl. No.: 13/799,999

(22) Filed: Mar. 13, 2013

(65) Prior Publication Data

US 2014/0269809 A1    Sep. 18, 2014

(51) Int. Cl.
*G01K 15/00* (2006.01)
*G01N 25/18* (2006.01)

(52) U.S. Cl.
CPC .............. *G01K 15/005* (2013.01); *G01N 25/18* (2013.01); *G01K 15/002* (2013.01)

(58) Field of Classification Search
USPC ............................ 73/25.03; 374/1, 36, 31, 43
See application file for complete search history.

(56) References Cited

U.S. PATENT DOCUMENTS

| | | | |
|---|---|---|---|
| 1,715,374 A * | 6/1929 | Krueger ........................ | 73/25.03 |
| 3,519,391 A | 7/1970 | Winter et al. | |
| 4,215,564 A * | 8/1980 | Lawson et al. ............... | 73/25.04 |
| 4,804,632 A | 2/1989 | Schuck et al. | |
| 4,859,078 A * | 8/1989 | Bowman et al. ................. | 374/44 |
| 4,970,891 A | 11/1990 | Blevins et al. | |
| 5,311,447 A | 5/1994 | Bonne | |
| 5,356,819 A | 10/1994 | Ritschel | |
| 5,756,878 A * | 5/1998 | Muto et al. .................... | 73/25.03 |
| 6,640,626 B2 | 11/2003 | Saikalis et al. | |
| 7,399,118 B2 * | 7/2008 | Matter et al. .................... | 374/36 |
| 7,937,984 B2 | 5/2011 | Tobias | |
| 8,161,795 B2 | 4/2012 | De Coulon et al. | |
| 8,302,459 B2 | 11/2012 | Matsuhama et al. | |
| 8,689,609 B2 * | 4/2014 | Oishi et al. .................... | 73/25.05 |
| 2005/0028580 A1 * | 2/2005 | Bauer et al. .................. | 73/25.03 |
| 2007/0169541 A1 * | 7/2007 | Norbeck et al. ............. | 73/25.03 |
| 2011/0077872 A1 | 3/2011 | Loui et al. | |
| 2011/0185789 A1 | 8/2011 | Ooishi et al. | |

OTHER PUBLICATIONS

International Search Report and Written Opinion for PCT/US13/030840 mailed Sep. 23, 2013, 10 pages.
ABB Inc., "NGC Calibration Techniques," Technical Bulletin 152, Totalflow Technical Bulletin, Version 1.0, Revision AA, Jul. 23, 2007, 9 pages.

* cited by examiner

*Primary Examiner* — Lisa Caputo
*Assistant Examiner* — Nasir U Ahmed
(74) *Attorney, Agent, or Firm* — Morgan, Lewis & Bockius LLP

(57) ABSTRACT

A method is provided for calibrating a thermal conductivity sensor in a first medium A from measurements in a second medium B. The method includes maintaining the sensor at a substantially fixed temperature $T_1$, and measuring a heat flux $I_B(T_1)$ from the thermal element in the second medium B. A corresponding heat flux $I_A(T_1)$ in the first medium A is calculated using known thermal conductivities of the first medium A and the second medium B.

8 Claims, 3 Drawing Sheets

GAS SENSORS AND METHODS OF CALIBRATING SAME

TECHNICAL FIELD

In various embodiments, the invention relates to sensors for detecting the presence of a target species in a gaseous medium and, more particularly, to methods of calibrating thermal conductivity sensors for measuring the concentration of methane ($CH_4$) in air.

BACKGROUND

Methane is a common gas that makes up a large proportion of natural gas, which is used for heating, cooking, and other applications. In its naturally occurring state, methane is odorless, tasteless, colorless, and non-toxic. In an enclosed space, however, methane may cause suffocation, if it displaces oxygen. Methane is also flammable and presents a risk of explosion if the gas is not detected and/or controlled.

One type of methane detector includes a thermal conductivity sensor that detects methane by measuring the thermal conductivity of a gaseous mixture. It is a universal practice to calibrate this sensor with pure methane. Calibration with pure methane requires an available methane supply and equipment for storing and delivering it. Also, suitable precautions (e.g. a laboratory exhaust hood, odorization, etc.) must be taken since pure methane raises potential safety concerns.

There is therefore a need for improved methods of calibrating thermal conductivity sensors for a target species (e.g., methane or propane) in a gaseous medium (e.g., air). In particular, there is a need for a method of calibrating such sensors without using the pure target species as a calibration gas.

SUMMARY OF THE INVENTION

In general, embodiments of the present invention feature a method of calibrating a thermal conductivity sensor for detecting a target species in a gaseous medium. Unlike previous methods that require the use of the pure target species (e.g., pure methane), embodiments of the method described herein utilize only ambient air for calibration. Accordingly, the new method is generally safer, less expensive and easier to perform. Furthermore, it can be performed anywhere, in the field as well as in a laboratory, thereby making field measurements more reliable.

In one aspect, embodiments of the invention relate to a method of calibrating a thermal conductivity sensor in a first medium A from measurements in a second medium B. The method includes maintaining the sensor at a substantially fixed temperature $T_1$, and measuring a heat flux $I_B(T_1)$ in the second medium B. A corresponding heat flux $I_A(T_1)$ in the first medium A is calculated using known thermal conductivities of the first medium A and the second medium B.

In certain embodiments, the first medium A includes methane, ethane, or propane, and the second medium B is or includes air. The fixed temperature $T_1$ may be, for example, in a range from about 70° C. to about 300° C. In some embodiments, the method also includes: measuring a heat flux $I_M(T_1)$ of the thermal conductivity sensor in a mixture of a species $S_A$ and the second medium B, the species $S_A$ corresponding to the first medium A; and calculating a concentration $C_A$ of the species $S_A$ in the mixture according to $$C_A = \frac{I_M(T_1) - I_B(T_1)}{I_A(T_1) - I_B(T_1)}.$$

In another aspect, embodiments of the invention relate to a thermal conductivity sensor for measuring a concentration $C_A$ of a species $S_A$ in a mixture of the species $S_A$ and a medium B. The sensor includes a thermal element and a processor. The processor is configured to execute instructions to: maintain the thermal element at a substantially fixed temperature $T_1$; measure a heat flux $I_B(T_1)$ from the thermal element in the medium B; and calculate a heat flux $I_A(T_1)$ from the thermal element in the species $S_A$. The heat flux $I_A(T_1)$ corresponds to the fixed temperature $T_1$ of the thermal element. The heat flux $I_A(T_1)$ is calculated based on the heat flux $I_B(T_1)$ and thermal conductivities of the species $S_A$ and the medium B at the fixed temperature $T_1$.

In certain embodiments, the species $S_A$ includes methane, ethane, or propane, and the medium B includes air. The fixed temperature $T_1$ may be in a range from, for example, about 70° C. to about 300° C. In some embodiments, the processor is configured to execute instructions to: measure a heat flux $I_M(T_1)$ from the thermal element in a mixture of the species $S_A$ and the medium B; and calculate a concentration $C_A$ of the species $S_A$ in the mixture according to $$C_A = \frac{I_M(T_1) - I_B(T_1)}{I_A(T_1) - I_B(T_1)}.$$

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art.

It should be understood that the order of steps or order for performing certain actions is immaterial so long as the invention remains operable. Moreover, two or more steps or actions may be conducted simultaneously or in the reverse order from that described here.

The mention herein of a publication, for example, in the Background section, is not an admission that it serves as prior art with respect to any of the claims presented herein. The Background section is presented for purposes of clarity and is not meant as a description of prior art with respect to any claim.

In general, the devices and methods described herein relate to the detection of a target species (e.g., methane) in a gaseous medium or mixture (e.g., air). Detection of the target species is understood to include or consist essentially of detecting the presence of the target species in the mixture and/or measuring a concentration (e.g., a volume or mole percent) of the target species in the mixture. The target species may be any type of gaseous species, including, for example, methane, ethane, propane, or natural gas. A particular target species is methane. The gaseous medium may include any gaseous species and in particular ambient air.

As mentioned, previous methods of calibrating thermal conductivity sensors for the detection of methane in air utilize pure methane as the calibration gas. It has been universally believed that pure methane is required for calibration to accurately determine methane in mixtures with air. In fact, it is presently discovered that calibration with pure methane is only required when the temperature of the thermal conductivity sensor is not controlled but allowed to vary as the thermal conductivity of the gas changes, as occurs, for example, when a Wheatstone Bridge or a similar electronic device is used for the measurements.

Advantageously, in accordance with certain embodiments, it is presently discovered that thermal conductivity sensors may be accurately calibrated using ambient air, rather than pure methane, as the calibration gas. In general, the calibration methods described herein may include predicting a response of the thermal conductivity sensor in a first medium (e.g., methane) based on measurements obtained in a second medium (e.g., ambient air).

Figure 1:
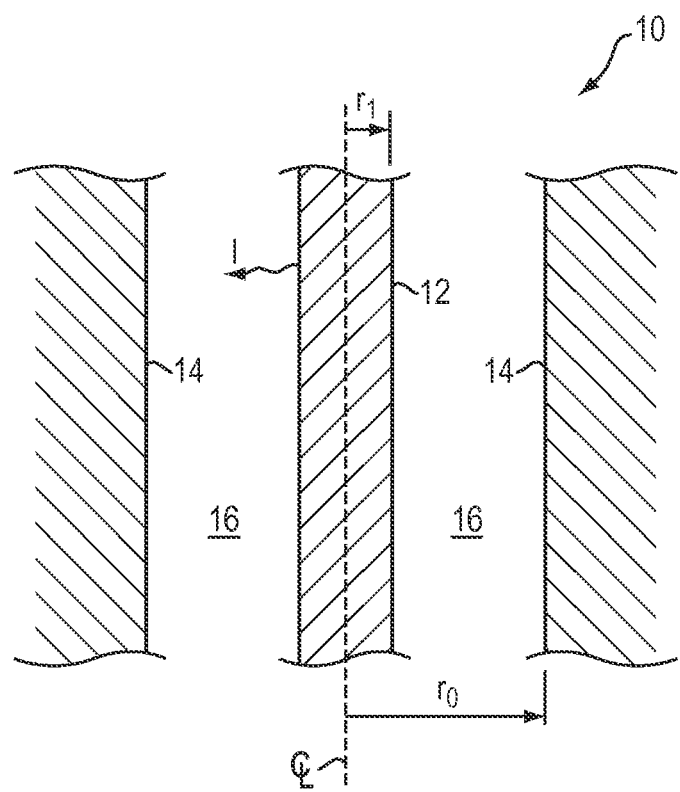
FIG. 1 is a schematic, side, cross-sectional view of a thermal conductivity sensor having a thermal element and a heat sink, in accordance with an illustrative embodiment of the invention.
Figure 2:
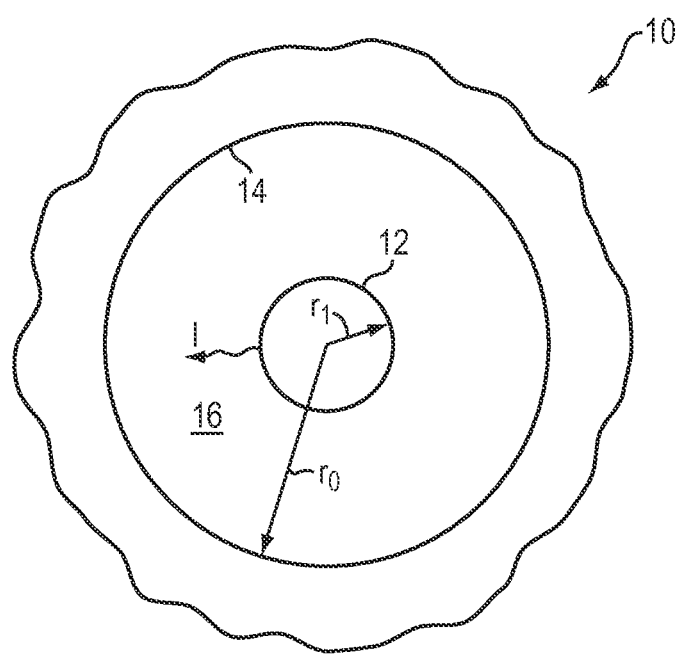
FIG. 2 is a schematic, top view of a thermal conductivity sensor having a thermal element and a heat sink, in accordance with an illustrative embodiment of the invention.

FIGS. 1 and 2 depict a thermal conductivity sensor 10 for measuring a concentration C of a target species (e.g., methane) in a mixture of gases (e.g., methane and air), in accordance with certain embodiments of the invention. The sensor includes a wire or thermal element 12 having an outer radius $r_1$ surrounded by a concentric heat sink 14 having an inner radius $r_0$. A region 16 between the thermal element 12 and the heat sink 14 is occupied by the gas mixture. To determine the concentration C of the target species in the mixture, the sensor 10 measures a conductive heat transfer rate through the mixture, from thermal element 12 to the heat sink 14. The measured heat transfer rate is then used to calculate a thermal conductivity of the mixture, and the concentration C is inferred or calculated from the thermal conductivity. The thermal element 12 is maintained at a fixed temperature when the heat transfer rate is measured.

In general, the thermal element 12 and/or the heat sink 14 may have any shape. For example, the thermal element 12 and/or the heat sink 14 may be substantially flat, curved, cylindrical, spherical, and/or combinations thereof. In the depicted embodiment, the thermal element and the heat sink are substantially cylindrical.

In general, heat flux values within the sensor may be measured using any available technique. A simple way is to measure the power required to keep the thermal element at a fixed temperature.

Referring again to the sensor 10 in FIGS. 1 and 2, the conductive heat flux, I, from the thermal element 12 to the heat sink 14 may be expressed as $$I = [T(r_1) - T(r_0)] \frac{2\pi l K}{\ln(r_0/r_1)} = (\text{constant})K,$$

where T is the temperature, l is the length of the wire, and K is the thermal conductivity of the medium. This last quantity is a bulk thermodynamic property of the medium, independent of the particular construction of the sensor. If the medium is air, the gas of interest (i.e., the target species) methane, and no other gases are present in significant quantities, and noting that methane and air form simple mixtures, the thermal conductivity of a methane and air mixture is $$K = C_A K_A + C_B K_B$$

where $C_A$ and $C_B$ are mole fractions of methane and air, and $K_A$ and $K_B$ are thermal conductivities of pure methane and air, respectively.

The thermal flux in pure air ($C_A=0$, $C_B=1$) is $$I_B = (\text{constant})K_B,$$

and in pure methane ($C_A=1$, $C_B=0$), $$I_A = (\text{constant})K_A,$$

and in a mixture of methane in air $$I_M = (\text{constant})(C_A K_A + C_B K_B).$$

Thus, a measurement of some unknown mixture compared to air is given by $$I_M - I_B = \text{constant}(C_A K_A + C_B K_B) - \text{constant}(K_B).$$

Noting that $C_B = 1 - C_A$, we have $$I_M - I_B = \text{constant}(C_A K_A + (1 - C_A)K_B - K_B)$$
$$= \text{constant}(C_A K_A - C_A K_B)$$
$$= (\text{constant})C_A(K_A - K_B).$$

Or substituting from the expressions for $I_A$ and $I_B$, above, $$I_M - I_B = C_A(I_A - I_B).$$

If $C_A=0$, then $I_M=I_B$, and this is the zero of the sensor (pure ambient air). If, on the other hand, $C_A=1$, then $I_M=I_A$, and this is the upper limit of the sensor (pure methane). For all other cases, $$C_A = \frac{I_M - I_B}{I_A - I_B}$$

or, using the more familiar units of volume percent, $$\% \text{ Vol } C_A = (I_M - I_B) \times \frac{100}{I_A - I_B}.$$

Generally, the quantity $I_A - I_B$ is referred to as the Gain of the sensor.

Figure 3:
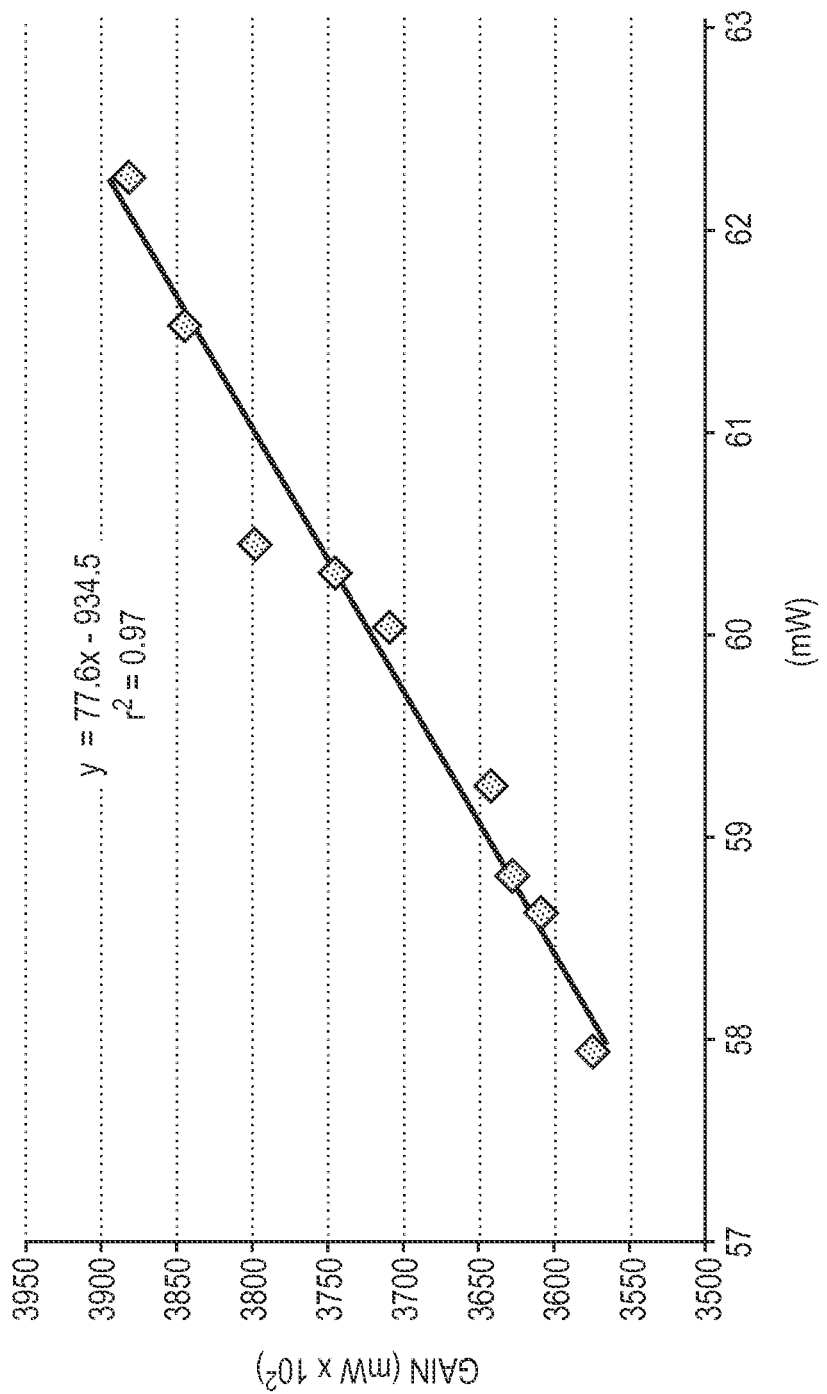
FIG. 3 is a plot of sensor gain versus heat flux through air, for a thermal conductivity sensor, in accordance with an illustrative embodiment of the invention.

The relation between Gain and the thermal flux in air for several methane sensors, corrected for variation in ambient temperature, is shown in FIG. 3. As expected, the thermal flux for the sensors is substantially linearly related to the sensor Gain. A best fit slope through the data in the Figure is 0.77, with a correlation coefficient of $r^2$=0.97. At the temperature of the measurement, 280° C., the thermal conductivity of air is 43 mW/mK (milliwatts per meter degree kelvin) and that for pure methane is 76 mW/mK. Therefore, we expect $$I_A = \frac{76}{43} I_B + \text{constant}$$

Or $$I_A - I_B = 0.77 I_B + \text{constant},$$

in good agreement with the data in the Figure. In summary, the measured heat flux $I_B$ in air may be used to compute the sensor's response in pure methane, thereby making calibration with pure methane unnecessary.

It should be emphasized that the analysis above applies only when the temperature of the thermal element is maintained at a constant or substantially constant value, e.g., by using an electronic feedback circuit together with appropriate high speed converters for control. In general, if a bridge or other simple electronic circuit operating with a fixed current is employed, the temperature of the thermal element is not fixed, and the above analysis is not applicable.

In certain embodiments, the sensors described herein include a memory that can be read by a processor. The memory may include computer storage media in the form of volatile and/or nonvolatile memory such as read only memory (ROM) and random access memory (RAM). The processor executes instructions that are stored in order to process data and carry out the methods described herein. The set of instructions may include various instructions that perform a particular task or tasks. Such a set of instructions for performing a particular task may be characterized as a program, software program, software, engine, module, component, mechanism, or tool.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A method of calibrating a thermal conductivity sensor in a first medium A from measurements in a second medium B consisting of air free of any gaseous species of the medium A, the method comprising:

maintaining the sensor at a substantially fixed temperature $T_1$;

during the maintaining step, measuring a heat flux $I_B(T_1)$ in the second medium B;

calculating a corresponding heat flux $I_A(T_1)$ in the first medium A, from (i) the measured heat flux in the second medium B and (ii) known thermal conductivities of the first medium A and the second medium B; and based on the calculation, calibrating the sensor for measurements of a mixture of medium A and medium B by relating measurements of the heat flux $I_B(T_1)$ to the corresponding heat flux $I_A(T_1)$, thereby facilitating measurement, using the sensor, of a concentration of medium A in the mixture based on a measured heat flux of the mixture, the heat flux $I_A(T_1)$, and the heat flux $I_B(T_1)$.

2. The method of claim 1, wherein the first medium A comprises a member selected from the group consisting of methane, ethane, and propane.

3. The method of claim 1, wherein the fixed temperature $T_1$ is in a range from about 70° C. to about 300° C.

4. The method of claim 1, further comprising:

measuring a heat flux $I_M(T_1)$ of the thermal conductivity sensor in a mixture of a species $S_A$ and the second medium B, the species $S_A$ corresponding to the first medium A; and calculating a concentration $C_A$ of the species $S_A$ in the mixture based on the heat flux $I_M(T_1)$, the heat flux $I_A(T_1)$, and the heat flux $I_B(T_1)$, according to $$C_A = \frac{I_M(T_1) - I_B(T_1)}{I_A(T_1) - I_B(T_1)}.$$

5. A thermal conductivity sensor for measuring a concentration $C_A$ of a species $S_A$ in a mixture of the species $S_A$ and a medium B consisting of air, the sensor comprising:

a thermal element; and a processor configured to execute instructions stored in a non-transitory computer-readable medium to:

maintain the thermal element at a substantially fixed temperature $T_1$;

with the thermal element maintained at the substantially fixed temperature, measure a heat flux $I_B(T_1)$ from the thermal element in the medium B free of the species $S_A$; and calculate a heat flux $I_A(T_1)$ from the thermal element in the species $S_A$, the heat flux $I_A(T_1)$ corresponding to the fixed temperature $T_1$ of the thermal element, wherein the heat flux $I_A(T_1)$ is calculated based on the heat flux $I_B(T_1)$ and thermal conductivities of the species $S_A$ and the $S_A$-free medium B at the fixed temperature $T_1$ to facilitate measurement, using the thermal element, of a concentration $C_A$ of the species $S_A$ in the mixture based on the heat flux $I_M(T_1)$, the heat flux $I_A(T_1)$, and the heat flux $I_B(T_1)$.

6. The sensor of claim 5, wherein the species $S_A$ comprises a member selected from the group consisting of methane, ethane, and propane.

7. The sensor of claim 5, wherein the fixed temperature $T_1$ is in a range from about 70° C. to about 300° C.

8. The sensor of claim 5, wherein the processor is configured to execute instructions to:

measure a heat flux $I_M(T_1)$ from the thermal element sensor in a mixture of the species $S_A$ and the medium B; and and calculate a concentration $C_A$ of the species $S_A$ in the mixture based on the heat flux $I_M(T_1)$, the heat flux $I_A(T_1)$, and the heat flux $I_B(T_1)$, according to $$C_A = \frac{I_M(T_1) - I_B(T_1)}{I_A(T_1) - I_B(T_1)}.$$

* * * * *